(12) United States Patent
Rothermel et al.

(10) Patent No.: US 9,669,178 B2
(45) Date of Patent: Jun. 6, 2017

(54) FLEXIBLE MEMBER ADJUSTABLE FOREHEAD SUPPORT

(75) Inventors: Justin Edward Rothermel, Monroeville, PA (US); Steven Charles Stegman, Gibsonia, PA (US); Karl Herbert Beitzel, Canton, OH (US); Jason Anthony Belton, Norton, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 361 days.

(21) Appl. No.: 14/117,634

(22) PCT Filed: May 16, 2012

(86) PCT No.: PCT/IB2012/052464
§ 371 (c)(1),
(2), (4) Date: Nov. 14, 2013

(87) PCT Pub. No.: WO2012/156929
PCT Pub. Date: Nov. 22, 2012

(65) Prior Publication Data
US 2014/0083428 A1    Mar. 27, 2014

Related U.S. Application Data

(60) Provisional application No. 61/486,984, filed on May 17, 2011.

(51) Int. Cl.
*A61M 16/06*    (2006.01)
*A61M 16/00*    (2006.01)
*A61M 16/08*    (2006.01)

(52) U.S. Cl.
CPC .... *A61M 16/0683* (2013.01); *A61M 16/0057* (2013.01); *A61M 16/06* (2013.01); *A61M 16/0655* (2014.02); *A61M 16/0875* (2013.01)

(58) Field of Classification Search
CPC .............. A61M 16/06; A61M 16/0605; A61M 16/0633; A61M 16/0638; A61M 16/0644;
(Continued)

(56) References Cited

U.S. PATENT DOCUMENTS 2,245,658 A * 6/1941 Erickson ............... A61M 16/06
                                                      128/206.28
5,176,515 A * 1/1993 Andrews .............. A61C 19/045
                                                         433/24
(Continued)

FOREIGN PATENT DOCUMENTS

CN    1905918 A    1/2007
CN    101389369 A    3/2009
(Continued)

*Primary Examiner* — (Jackie) Tan-Uyen T Ho
*Assistant Examiner* — Joseph D Boecker
(74) *Attorney, Agent, or Firm* — Michael W. Haas (57) ABSTRACT

A patient interface device includes a patient sealing assembly having a cushion and a frame member having a faceplate portion and an extension portion extending from the faceplate portion. The cushion is coupled to the faceplate portion. A forehead member engages the forehead of the patient, and a flexible elongated member is coupled to the extension portion. A drive assembly selectively causes the second end portion of the flexible elongated member to move relative to the extension portion in a first direction. Movement of the flexible elongated member relative to the extension portion in the first direction causes movement of the frame member relative to the forehead member in a second direction transverse to the first direction.

8 Claims, 9 Drawing Sheets

(58) Field of Classification Search
CPC ............ A61M 16/065; A61M 16/0655; A61M 16/0683; A61M 16/0875
USPC ............ 128/201.22–201.24, 205.25, 206.21, 128/206.24, 206.26–206.28, 207.11, 128/207.13, 207.18, 912; 2/181.8, 182.3, 2/183
See application file for complete search history.

(56) References Cited

U.S. PATENT DOCUMENTS

| | | | | |
|---|---|---|---|---|
| 5,558,090 | A * | 9/1996 | James | A61M 16/0488 128/207.17 |
| 7,819,119 | B2 * | 10/2010 | Ho | A61M 16/06 128/201.22 |
| 2003/0062048 | A1 * | 4/2003 | Gradon | A61M 16/06 128/207.11 |
| 2003/0075182 | A1 * | 4/2003 | Heidmann | A61M 16/06 128/207.11 |
| 2003/0084904 | A1 * | 5/2003 | Gunaratnam | A61M 16/06 128/206.27 |
| 2004/0045551 | A1 * | 3/2004 | Eaton | A61M 16/06 128/206.21 |
| 2004/0055352 | A1 * | 3/2004 | Lottner | B21C 1/00 72/278 |
| 2004/0182398 | A1 * | 9/2004 | Sprinkle | A61M 16/06 128/207.13 |
| 2004/0255949 | A1 * | 12/2004 | Lang | A61M 16/06 128/206.21 |
| 2005/0011521 | A1 * | 1/2005 | Sprinkle | A61M 16/06 128/206.21 |
| 2005/0022820 | A1 * | 2/2005 | Kwok | A61M 16/06 128/206.21 |
| 2005/0072428 | A1 * | 4/2005 | Ho | A61M 16/06 128/205.25 |
| 2005/0155603 | A1 * | 7/2005 | Frerichs | A61M 16/0633 128/206.21 |
| 2007/0044804 | A1 * | 3/2007 | Matula, Jr. | A61M 16/06 128/206.21 |
| 2007/0215161 | A1 * | 9/2007 | Frater | A61M 16/06 128/206.24 |
| 2008/0053446 | A1 * | 3/2008 | Sleeper | A61M 16/06 128/205.25 |
| 2008/0066761 | A1 * | 3/2008 | Hodos | A61M 16/06 128/206.28 |
| 2008/0135050 | A1 * | 6/2008 | Hitchcock | A61M 16/06 128/207.11 |
| 2010/0000542 | A1 * | 1/2010 | Chu | A61M 16/06 128/206.21 |
| 2010/0275923 | A1 * | 11/2010 | Guney | A44B 11/266 128/207.13 |
| 2011/0048425 | A1 * | 3/2011 | Chang | A61M 16/06 128/206.24 |
| 2012/0000463 | A1 * | 1/2012 | Bordewick | A61M 16/00 128/201.23 |
| 2012/0111333 | A1 * | 5/2012 | Eifler | A61M 16/0683 128/205.25 |
| 2012/0167879 | A1 * | 7/2012 | Bowman | A61M 16/0066 128/201.22 |
| 2014/0000617 | A1 * | 1/2014 | Rothermel | A61M 16/06 128/205.25 |
| 2014/0000618 | A1 * | 1/2014 | Belton | A61M 16/06 128/205.25 |

FOREIGN PATENT DOCUMENTS

| | | |
|---|---|---|
| CN | 101472637 A | 7/2009 |
| EP | 2005985 A2 | 12/2008 |
| EP | 2005986 A2 | 12/2008 |
| WO | WO2005068002 A1 | 7/2005 |
| WO | WO2005123166 A1 | 12/2005 |
| WO | WO2006074517 A1 | 7/2006 |
| WO | WO2007143793 A1 | 12/2007 |

* cited by examiner

FLEXIBLE MEMBER ADJUSTABLE FOREHEAD SUPPORT

REFERENCE TO RELATED APPLICATIONS

This patent application claims the priority benefit under 35 U.S.C. §371 of international patent application no. PCT/IB2012/052464, filed May 16, 2016, which claims the priority benefit under 35 U.S.C. §119(e) of U.S. Provisional Application No. 61/486,984 filed on May 17, 2011, the contents of which are herein incorporated by reference.

BACKGROUND OF THE INVENTION

1. Field of the Invention

The present invention relates to patient interface devices for transporting a gas to and/or from an airway of a user, and in particular, to a patient interface device including a mechanism for adjusting a forehead support of the patient interface device.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Because such patient interface devices are typically worn for an extended period of time, it is important for the headgear to maintain the mask component of the device in a tight enough seal against the patient's face without discomfort. One area where fit and comfort is often a concern is the bridge of the patient's nose, as most patient interface devices will apply a pressure to this area. If this pressure is not able to be managed effectively, either or both of a poor fit or patient discomfort will result, thereby limiting the effectiveness of the device.

SUMMARY OF THE INVENTION

In one embodiment, a patient interface device is provided that includes a patient sealing assembly adapted to communicate a flow of breathing gas within an airway of the patient, the patient sealing assembly including a cushion and a frame member having a faceplate portion and an extension portion extending from the faceplate portion, the cushion being coupled to the faceplate portion. The patient interface device also includes a forehead member structured to engage the forehead of the patient, an flexible elongated member having a first end portion and a second end portion, the first end portion being coupled to the forehead member and the second end portion being coupled to the extension portion of the frame member. A drive assembly is coupled to the second end portion of the elongated member. The drive assembly is structured to selectively cause the second end portion of the flexible elongated member to move relative to the extension portion of the frame member in a first direction. Movement of the elongated member relative to the extension portion in the first direction causes movement of the frame member relative to the forehead member in a second direction transverse to the first direction.

In another embodiment, a patient interface device is provided that includes a patient sealing assembly adapted to communicate a flow of breathing gas within an airway of a patient, the patient sealing assembly including a cushion and a frame member coupled to the cushion, a forehead member structured to engage the forehead of the patient, a flexible elongated member having a first end portion and a second end portion, the first end portion being coupled to the forehead member and the second end portion being coupled to the frame member, and a shaping form. The flexible elongated member is moveably received through the shaping form. The shaping form is structured change a shape of a selected portion of the elongated member when the selected portion is moved through the shaping form. Movement of the selected portion through the shaping form causes movement of the frame member relative to the forehead member.

In still another embodiment, a patient interface device is provided that includes a patient sealing assembly adapted to communicate a flow of breathing gas within an airway of a patient, the patient sealing assembly including a cushion and a frame member coupled to the cushion, a forehead member structured to engage a forehead of the patient, and a serrated belt member having a first end portion and a second end portion, the first end portion being coupled to the forehead member and the second end portion being moveably coupled to the frame member. The belt member has a plurality of notches provided on a portion of a surface thereof, the notches being structured to enable the belt member to bend at the portion of the surface, wherein movement of the second end portion of the belt member relative to the frame member causes movement of the frame member relative to the forehead member.

Accordingly, it is an object of the present invention to provide a patient interface device that overcomes the shortcomings of conventional patient interface devices. This object is achieved according to one embodiment of the present invention by providing a patient interface device that includes a selectively adjustable forehead support assembly that allows for simple and convenient management of the nose bridge pressure that is applied by the patient interface device.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
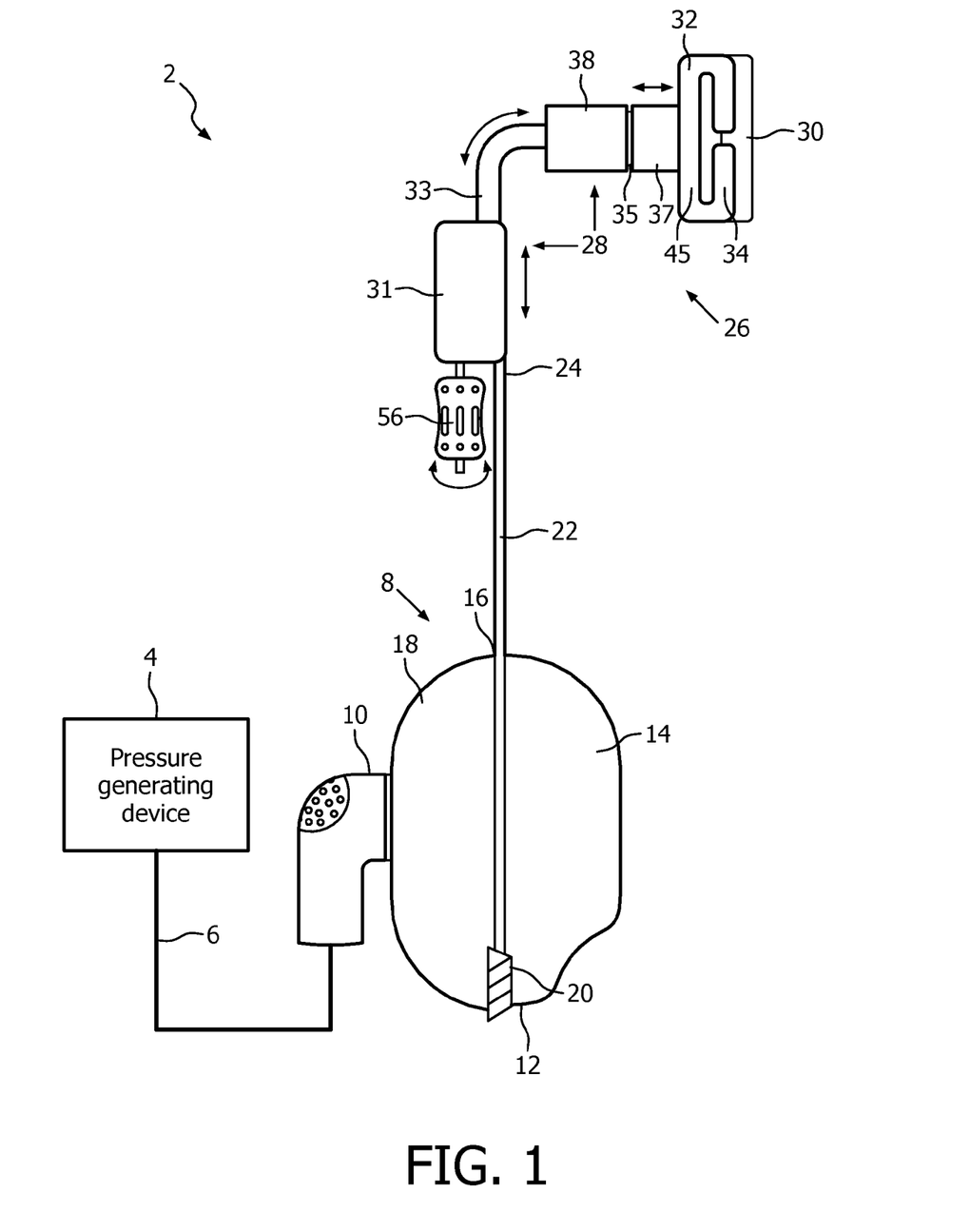
FIG. 1 is a side schematic diagram of a system adapted to provide a regimen of respiratory therapy to a patient according to one exemplary embodiment of the present invention.

A system 2 adapted to provide a regimen of respiratory therapy to a patient according to one exemplary embodiment is generally shown in FIG. 1. System 2 includes a pressure generating device 4, a delivery conduit 6, and a patient interface device 8 having a fluid coupling conduit 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8 through fluid coupling conduit 10, which in the illustrated embodiment is an elbow connector. Delivery conduit 6 and patient interface device 8 are often collectively referred to as a patient circuit. [27] Patient interface device 8 includes a patient sealing assembly 12, which in the illustrated embodiment is a nasal mask. However, other types of patient sealing assemblies, such as, without limitation, a nasal/oral mask or a nasal cushion, which facilitates the delivery of the flow of breathing gas to the airway of a patient may be substituted for patient sealing assembly 12 while remaining within the scope of the present invention. Patient sealing assembly 12 includes a cushion 14 coupled to a frame member 16. In the illustrated embodiment, cushion 14 is defined from a unitary piece of soft, flexible, cushiony, elastomeric material, such as, without limitation, silicone, an appropriately soft thermoplastic elastomer, a closed cell foam, or any combination of such materials. Also in the illustrated embodiment, frame 16 is made of a rigid or semi-rigid material, such as, without limitation, an injection molded thermoplastic or silicone, and includes a faceplate portion 18 to which cushion 14 is fluidly attached. An opening in faceplate portion 18, to which fluid coupling conduit 10 is coupled, allows the flow of breathing gas from pressure generating device 4 to be communicated to an interior space defined by cushion 14, and then to the airway of a patient. In addition, in the exemplary embodiment, faceplate portion 18 includes socket type connecting members 20 on opposite sides thereof for receiving a ball connector of a respective strap of a headgear component (not shown) to secure patient interface device 8 to the patient's head.

Frame member 16 also includes an elongated connecting member 22 having a distal end 24 that is connected to an adjustable forehead support assembly 26 of patient interface device 8. Adjustable forehead support assembly 26 includes an adjustment mechanism 28 that is coupled to a forehead cushion 30, which in the exemplary embodiment is made of a material that is similar to the material of cushion 14.

Figure 2:
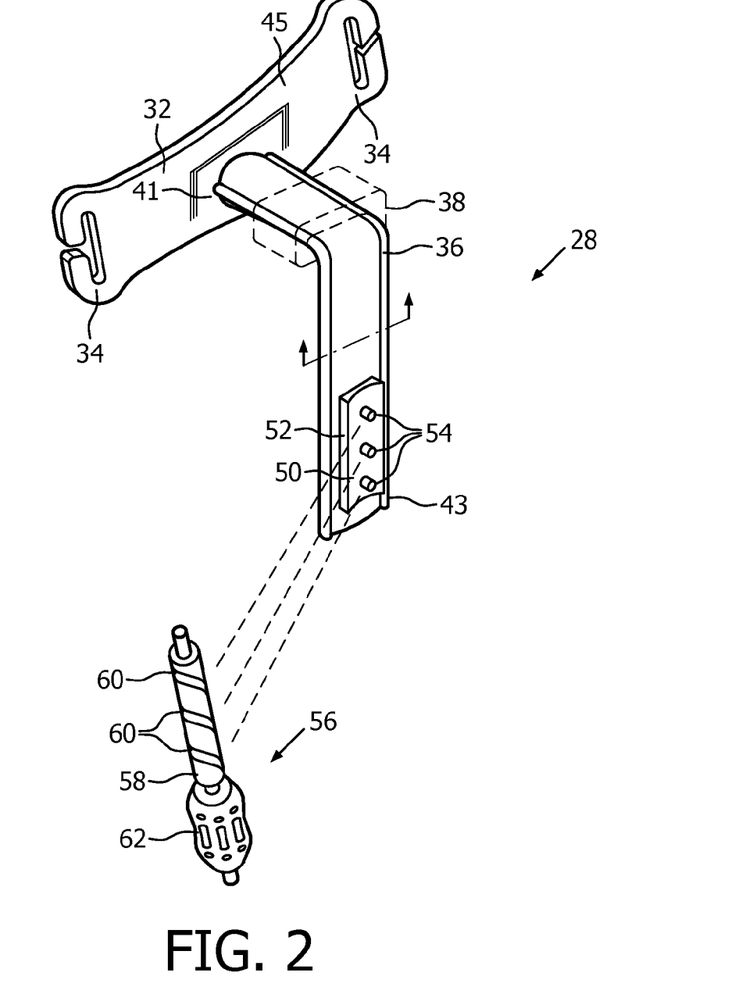
FIG. 2 is a schematic diagram showing certain components of an adjustment mechanism of the patient interface device of the system of FIG. 1.
Figure 3:
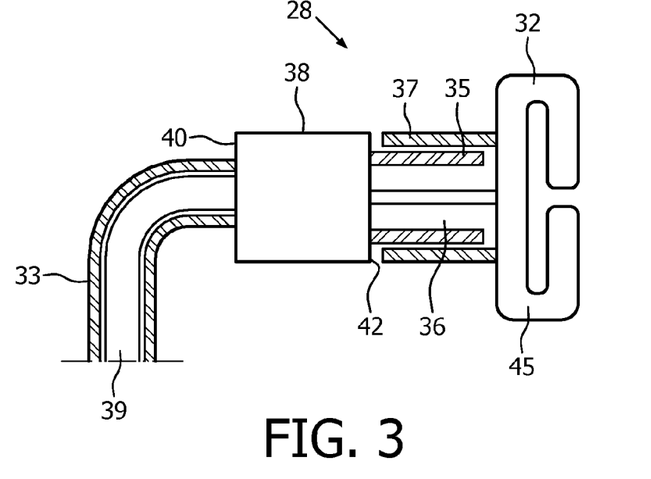
FIG. 3 is a side view in partial cross-section showing certain other components of an adjustment mechanism of the patient interface device of the system of FIG. 1.

FIG. 2 is a schematic diagram showing certain components of adjustment mechanism 28 and FIG. 3 is a side view in partial cross-section showing certain other components of adjustment mechanism 28 according to the exemplary embodiment of the present invention. As described in detail herein, adjustment mechanism 28 provides a mechanism for selectively adjusting the force applied to the bridge of the nose of a patient by an apex portion of cushion 14 by varying the position of frame member 16, and in particular distal end 24 thereof, with respect to forehead cushion 30.

Referring to FIGS. 1, 2, and 3, adjustment mechanism 28 includes a forehead cushion support member 32 to which forehead cushion 30 is attached. Forehead cushion support member 32 includes connecting elements 34 on either side thereof, each for receiving a respective top strap of a headgear component. It is to be understood that the present invention contemplates using any configuration for the headgear strap attachment to cushion support member 32, or omitting any attachment of the headgear strap to the cushion support member.

Figure 4:
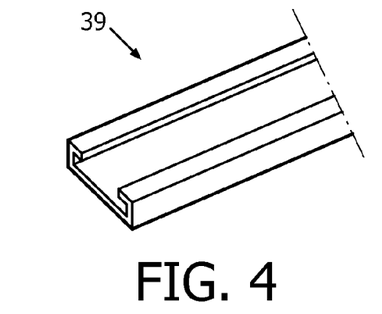
FIG. 4 is an isometric view of a guide track of the patient interface device of the system of FIG. 1

Adjustment mechanism 28 further includes a housing 31 that is coupled to the distal end 24 of frame member 16. As described elsewhere herein, housing 31 houses certain of the operational components of adjustment mechanism 28. Adjustment mechanism 28 also includes a support sleeve 33, a shaping form 38, an inner sleeve 35, an outer sleeve 37, and a guide track 39 having the form shown in FIG. 4 (for the sake of clarity and ease of illustration, inner sleeve 35 and outer sleeve 37 are not shown in FIG. 2, and shaping form 38 is shown in phantom lines in FIG. 2). More specifically, support sleeve 33 extends from housing 31 to a front surface 40 of shaping form 38, and guide track 39 extends within and is supported by support sleeve 33. Also, a first end of guide track 39 extends to front surface 40 of shaping form 38, and a second, opposite end of guide track 39 is affixed to housing 31 and thus frame member 16.

The purpose and function of guide track 39 is described elsewhere herein. Furthermore, inner sleeve 35 extends from a rear surface 42 of shaping form 38, and outer sleeve 37 extends from a front face 45 of forehead cushion support member 32. As shown in FIG. 3, inner sleeve 35 is provided inside outer sleeve 37 in a manner wherein those two components are able to move relative to one another (in a telescoping fashion) when frame member 16 and forehead cushion support member 32 are caused to move relative to one another as described in detail elsewhere herein. In the exemplary embodiment, support sleeve 33, inner sleeve 35, outer sleeve 37, and guide track 39 are each made of a rigid or semi-rigid material such as a suitable plastic.

Figure 5:
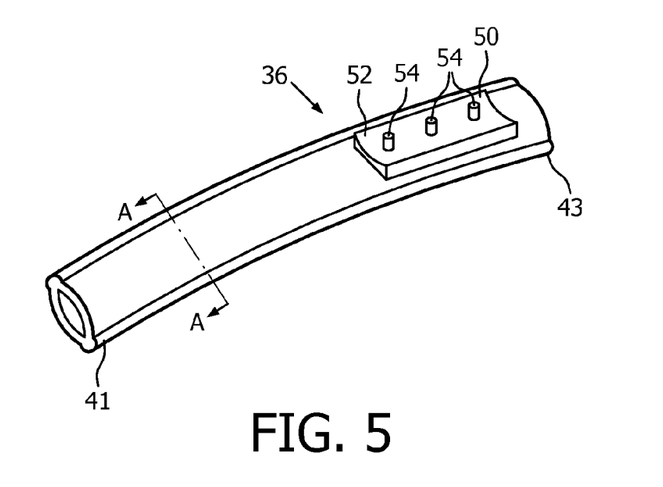
FIG. 5 is an isometric view of a tubular member of the patient interface device of the system of FIG. 1.

In addition, as seen in FIGS. 2 and 3, adjustment mechanism 28 also includes an elongated flexible tubular member 36. FIG. 5 is an isometric view of tubular member 36 according to an exemplary embodiment of the present invention. Tubular member 36 is made of a flexible (bendable) yet resilient material or combination of materials, such as, without limitation, polypropylene, polyethylene, or a non-thermoplastic material, that is able to return to substantially its original shape after passing back and forth through shaping form 38 as described herein. Tubular member 36 includes a first end 41 and a second end 43. First end 41 is affixed to front face 45 of forehead cushion support member 32. The reminder of the body of tubular member 36 is received within and extends through inner sleeve 35 and an outer sleeve 37, shaping form 38, support sleeve 33 and housing 31. In addition, within support sleeve 33, the body of flexible tubular member 36 is slideably received and held within guide track 39. The significance of this feature is explained elsewhere herein.

Figure 6:
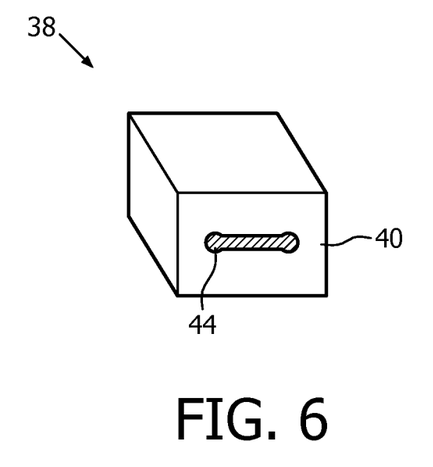
FIGS. 6 and 7 are front and rear isometric views of a shaping form of the patient interface device of the system of FIG. 1.
Figure 7:
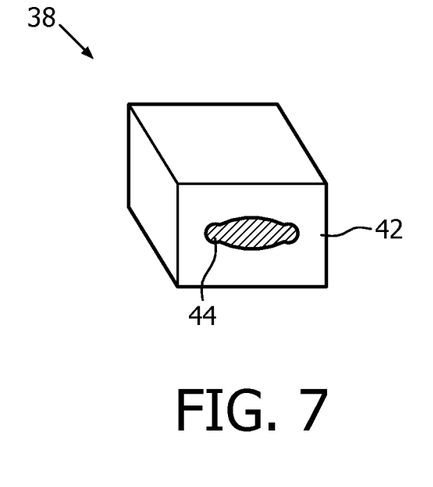

FIGS. 6 and 7 are front and rear isometric views, respectively, of shaping form 38 according to an exemplary embodiment of the present invention. In the exemplary embodiment, shaping form 38 is made of a rigid material such as, without limitation, a plastic (e.g., thermoplastic) or a metal. As seen in FIGS. 6 and 7, shaping form 38 has a cuboid shape and defines an internal shaping surface 44 that is structured to transform the outer shape of a component made from a formable material that is passed therethough from a first shape to a second shape depending on the direction in which it is passed. In particular, if a component having an initial outer shape that is in the form shown on front surface 40 is passed from the front surface 40 to the rear surface 42, its outer shape will be transformed from that initial shape to the shape that is shown on rear surface 44. Conversely, if a component having an initial outer shape that is in the form shown on rear surface 42 is passed from the rear surface 42 to the front surface 40, its outer shape will be transformed from that initial shape to the shape that is shown on front surface 40.

Figure 8:
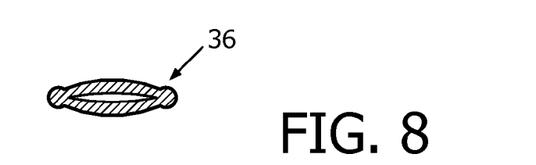
FIGS. 8 and 9 are cross-sectional views of the tubular member of the patient interface device of the system of FIG. 1.
Figure 9:
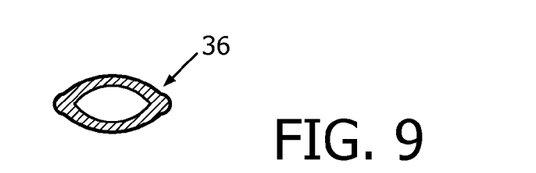

Referring again to FIG. 5, flexible tubular member 36 initially has a generally flat profile having the cross-sectional shape shown in FIG. 8, which cross-section is taken along lines A-A of FIGS. 2 and 5. As seen in FIG. 8, the initial cross-sectional shape of flexible tubular member 36 matches the shape that is present on front surface 40 of shaping form 38. Thus, if tubular member 36 were to be passed through shaping form 38 from the front surface 40 to the rear surface 42, the cross-sectional shape thereof will be transformed from the shape shown in FIG. 8 to the cross-sectional shape shown in FIG. 9, which matches the shape that is present on rear surface 42 of shaping form 38. In addition, portions of tubular member 36 having the shape of FIG. 8 are generally not self-supporting, while portions of tubular member 36 having the shape of FIG. 9 have sufficient structural integrity to be self-supporting (i.e., able to retain its shape without bending or deforming). The significance of this feature to the operation of adjustment mechanism 28 is explained below.

In addition, as seen in FIGS. 2 and 5, the top surface of second end 43 of tubular member 36 has a drive beam 50 provided thereon. Drive beam 50 includes a base 52 having a number of posts 54 extending therefrom. In the exemplary embodiment shown in FIGS. 2 and 5, three posts 54 are provided on base 52, although more or less posts 54 may also be utilized.

Referring to FIGS. 1 and 2, adjustment mechanism 28 also includes a drive screw 56 that is structured to be cooperatively engaged with drive beam 50. More specifically, drive screw 56 includes a cylindrical body 58 having a spiral groove 60 provided therein. A knob 62 is provided at a bottom end of cylindrical body 58. Posts 54 are structured to be received within spiral groove 60 such that when drive screw 56 is rotated, it will move drive beam 50, and flexible tubular member 36 attached thereto, back and forth in a direction that is parallel to the longitudinal axis of drive beam 50.

To assemble adjustment mechanism 28, flexible tubular member 36 in its initial condition (FIG. 5) is inserted into guide track 39 within housing 31 and is passed through guide track 39 and support sleeve 33 to front surface 40 of shaping form 38. Guide track 39 supports tubular member and ensures that is does not buckle as it is slid within guide track 39 (as noted elsewhere herein, tubular member 36 is not self-supporting in its initial condition). The first end 41 of flexible tubular member 36 is then passed through shaping form 38 from the front surface 40 to the rear surface 42. As a result, the cross-sectional shape of that portion of tubular member 36 will be transformed from the shape shown in FIG. 8 to the cross-sectional shape shown in FIG. 9. The first end 41 of flexible tubular member 36 then passes within inner sleeve 35 and outer sleeve 37 and is attached to front face 45 of forehead cushion support member 32 using a suitable mechanism, such as an adhesive or by mounting it on a post (not shown) extending outwardly from front face 45.

Drive screw 56 is then placed into engagement with drive beam 50 as described elsewhere herein. In the exemplary embodiment, drive screw 56 is securely and rotateably held by housing 31 in a manner which places and holds drive screw 56 in a position wherein it is able to engage and drive beam 50.

Thus, when patient interface device 8 is assembled as just described, the position of connecting member 22 of frame member 16 relative to forehead cushion support member 32 and forehead cushion 30 (which will be at a fixed position on the patient's head) can be adjusted by operation of the adjustment mechanism 28. In particular, rotation of knob member 56 will cause flexible tubular member 36 to be moved within guide track 39 (in a direction that is parallel to the longitudinal axis of connecting member 22). When this is done in a forward direction, portions of flexible tubular member 36 will be forced through shaping form 38 and converted to the generally self-supporting shape of FIG. 9. This will also effectively lengthen the distance from the distal end of frame member 16 to forehead cushion support member 32.

Because forehead cushion support member 32 and forehead cushion 30 are at a fixed position on the patient's head, such lengthening will cause the position of the connected elements including the distal end 24, support sleeve 33, guide track 39, shaping form 38, and an inner sleeve 35 relative to forehead cushion support member 32 and forehead cushion 30 to be changed. The reverse effect can be achieved by rotating knob member 56 in the other direction, effectively shortening the distance described above. This selective adjustment thus allows for selective adjustment of the force that is applied to the bridge of the patient's nose by the apex portion of cushion 14 because varying the position of frame member 16 as just described will cause the apex portion of cushion 14 to rotate toward and away from the patient' nose.

Figure 10:
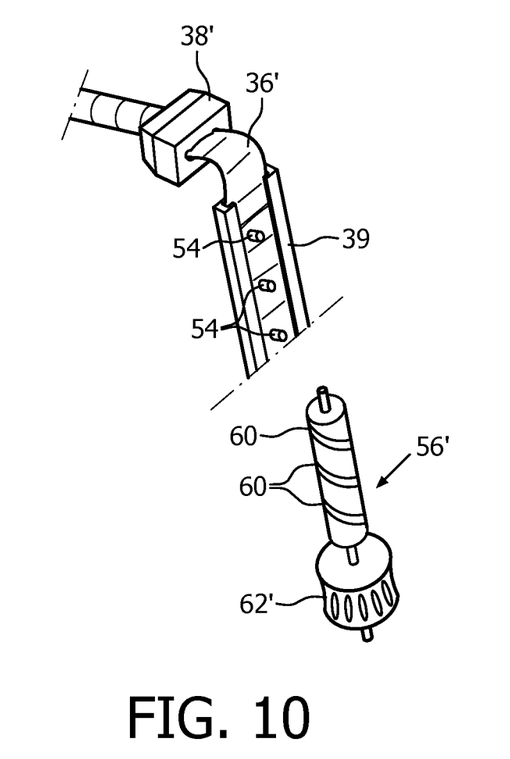
FIGS. 10 and 11 are schematic diagrams showing certain components of an alternative adjustment mechanism that may be used in the patient interface device of the system of FIG. 1.
Figure 11:
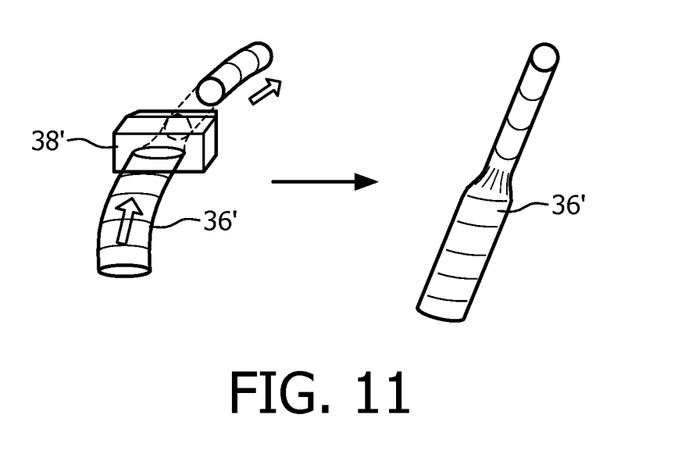

FIGS. 10 and 11 show an alternative tubular member 36', an alternative shaping form 38', and an alternative drive screw 56'. These alternative components, while having a slightly different form, shape or configuration as the corresponding components shown in FIGS. 1-9, perform substantially the same function as those components and thus may be substituted therefor in system 2.

Figure 12:
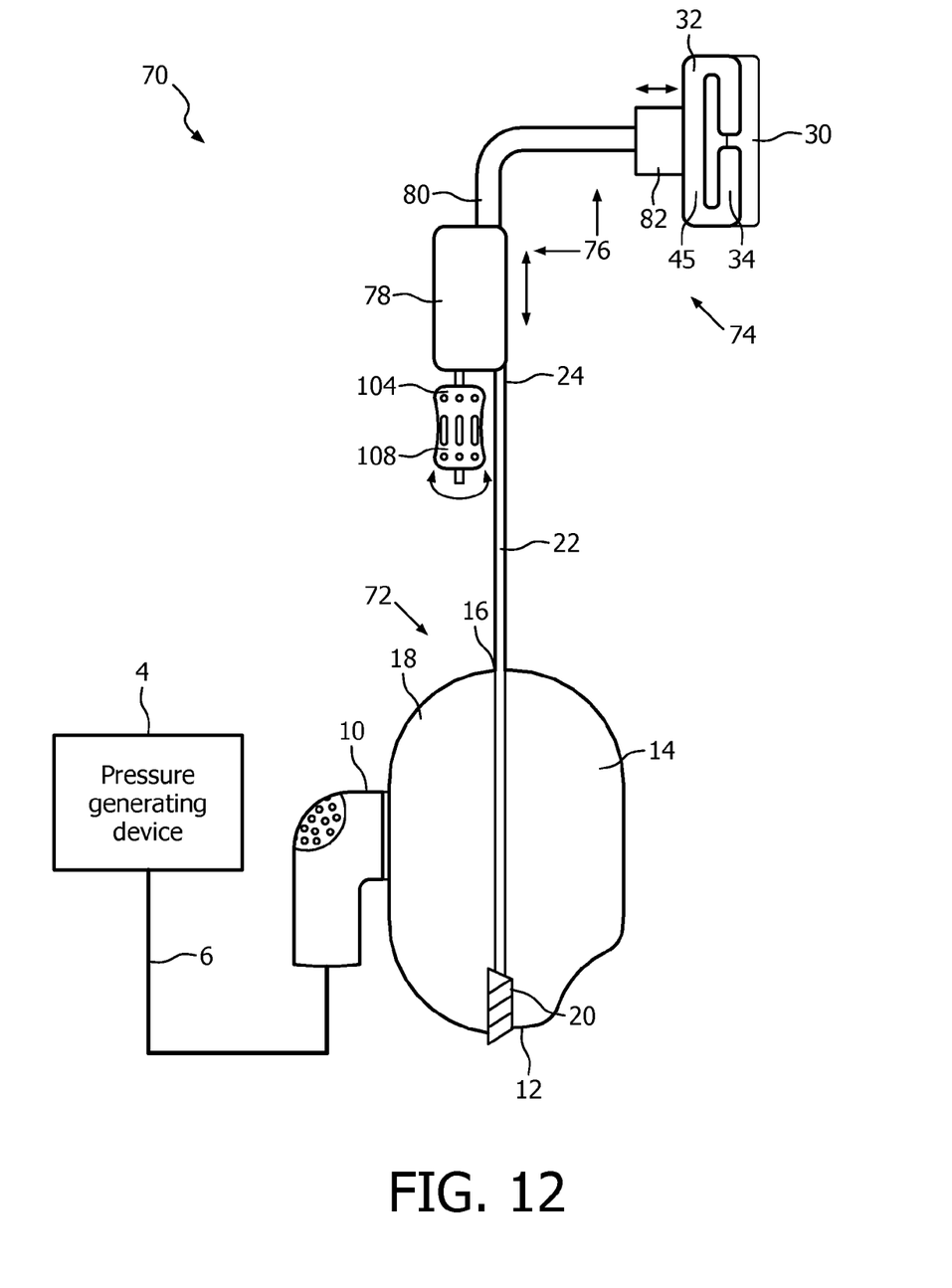
FIG. 12 is a side schematic diagram of a system adapted to provide a regimen of respiratory therapy to a patient according to another exemplary embodiment of the present invention.

A system 70 adapted to provide a regimen of respiratory therapy to a patient according to an alternative exemplary embodiment is generally shown in FIG. 12. System 70 includes many of the same components as system 2 described above, and like components are labeled with like reference numerals. More specifically, system 70 includes a pressure generating device 4, a delivery conduit 6, and an alternative patient interface device 72. As described elsewhere herein, delivery conduit 6 is structured to communicate a flow of breathing gas from pressure generating device 4 to patient interface device 72 through fluid coupling conduit 10, which in the illustrated embodiment is an elbow connector.

Patient interface device 72 includes a patient sealing assembly as described elsewhere herein that includes a cushion 14 coupled to a frame member 16 having a faceplate portion 18 to which cushion 14 is fluidly attached. An opening in faceplate portion 18, to which fluid coupling conduit 10 is coupled, allows the flow of breathing gas from pressure generating device 4 to be communicated to an interior space defined by cushion 14, and then to the airway of a patient. In addition, frame member 16 includes an elongated connecting member 22 having a distal end 24 that is connected to an adjustable forehead support assembly 74, described below, of patient interface device 8.

Figure 13:
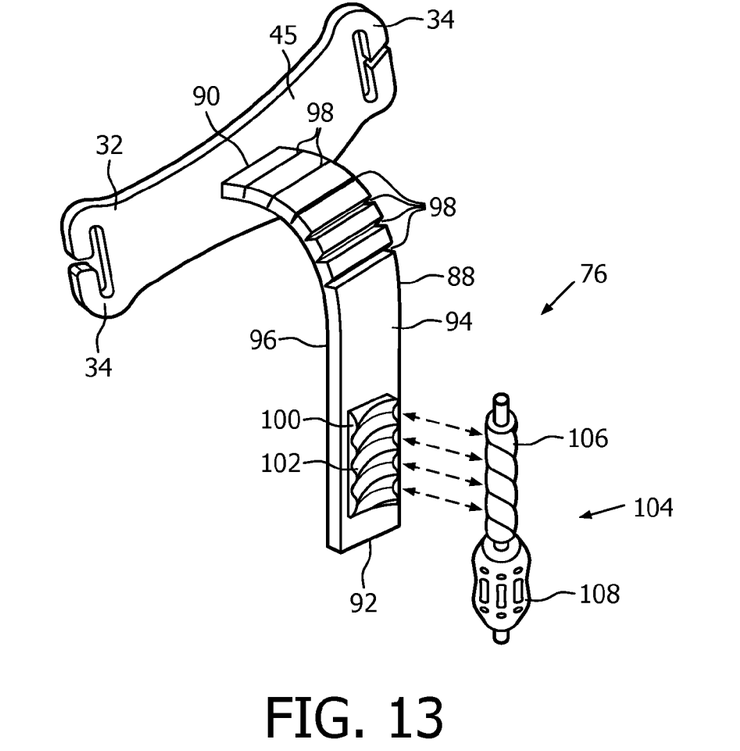
FIG. 13 is a schematic diagram showing certain components of an adjustment mechanism of the patient interface device of the system of FIG. 12.
Figure 14:
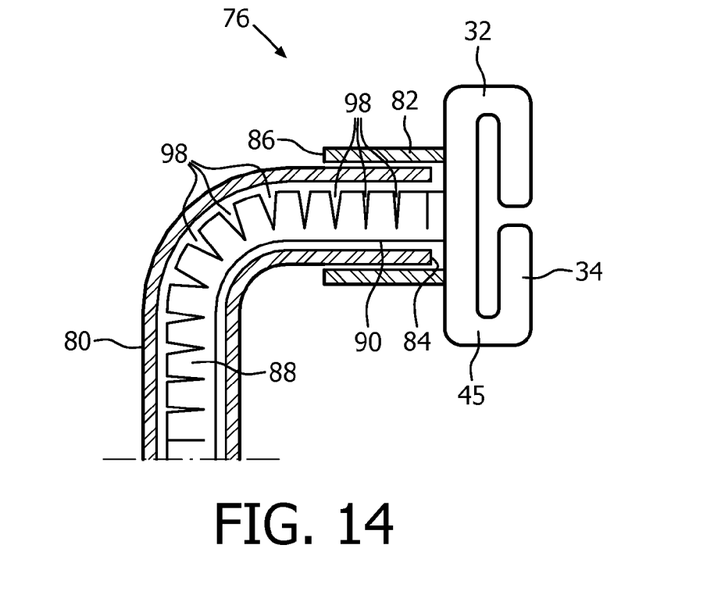
FIG. 14 is a side view in partial cross-section showing certain other components of an adjustment mechanism of the patient interface device of the system of FIG. 12.

Adjustable forehead support assembly 74 in this embodiment includes an adjustment mechanism 76 that is coupled to a forehead cushion 30 as described elsewhere herein. FIG. 13 is a schematic diagram showing certain components of adjustment mechanism 76 and FIG. 14 is a side view in partial cross-section showing certain other components of adjustment mechanism 76. As described in detail herein, adjustment mechanism 76 provides a mechanism for selectively adjusting the force applied to the bridge of the nose of a patient by an apex portion of cushion 14 by varying the position of frame member 16, and in particular distal end 24 thereof, with respect to forehead cushion 30.

Referring to FIGS. 12, 13 and 14, adjustment mechanism 76 includes a forehead cushion support member 32, described elsewhere herein, to which forehead cushion 30 is attached. Adjustment mechanism 76 further includes a housing 78 that is coupled to the distal end 24 of frame member 16. As described elsewhere herein, housing 78 houses certain of the operational components of adjustment mechanism 76. Adjustment mechanism 76 also includes a first support sleeve 80 and a second support sleeve 82 each made of a rigid or semi-rigid material such as a suitable plastic (for the sake of clarity and ease of illustration, inner sleeve 35 and outer sleeve 37 are not shown in FIG. 2, and shaping form 38 is shown in phantom lines in FIG. 2).

More specifically, first support sleeve 80 extends from housing 78 to an open end 84 positioned adjacent to forehead cushion support member 32 and, in the illustrated embodiment, has the curved shape as shown in FIGS. 12 and 14. Second support sleeve 82 extends from the front face 45 of forehead cushion support member 32 and terminates at an open end 86. As shown in FIG. 14, first support sleeve 80 s received within second support sleeve 82 in a manner wherein those two components are able to move relative to one another (in a telescoping fashion) when frame member 16 and forehead cushion support member 32 are caused to move relative to one another as described in detail elsewhere herein.

In addition, as seen in FIGS. 13 and 14, adjustment mechanism 28 also includes flexible, elongated belt member 88. In the exemplary embodiment, belt member 88 is a generally rectilinear member (although other shapes are also possible) that is made of a rigid or semi-rigid material, such as, without limitation, a thermoplastic or thermoset material. Belt member 88 may also be made of two materials co-bonded together, one for rigidity and one for flexibility. Belt member 88 includes a first end 90, a second end 92, a top surface 94 and a bottom surface 96. First end 90 is affixed to front face 45 of forehead cushion support member 32. The reminder of the body of flexible belt member 88 is received within and extends through first support sleeve 80 and second support sleeve 82 into housing 78.

In addition, while not shown in the illustrated embodiment, flexible belt member 88 may also be slideably received and held within a guide track 39, described elsewhere herein, that is received and held within first support sleeve 80. In addition, as seen in FIGS. 13 and 14, a portion of (e.g., the first third to half of) the top surface 94 of belt member 88 adjacent to first end 90 is serrated such that the top surface 94 includes serrations or notches 98 that extend into the body of body member. Such serrations or notches 98 enable the otherwise generally inflexible rigid or semi-rigid belt member 88 to bend as shown in FIGS. 13 and 14. The significance of this feature is explained below. In the exemplary embodiment, belt member 88 is about 0.15 to 0.20 inches thick, and the bottom fifteen to twenty thousands of an inch of the body of belt member 88 is solid and not serrated.

In addition, as seen in FIG. 13, the top surface of second end 92 of flexible belt member 88 has a drive beam 100 provided thereon. Drive beam 50 includes a worm gear train 102. Adjustment mechanism 76 also includes a drive screw 104 that is structured to be cooperatively engaged with drive beam 50. More specifically, drive screw 104 includes a worm screw member 106 and a knob 108 provided at a bottom end of worm screw member 106. Worm screw member 106 is structured to engage worm gear train 102 such that when drive screw 104 is rotated, it will move drive beam 100, and flexible belt member 88 attached thereto, back and forth in a direction that is parallel to the longitudinal axis of drive beam 100. In the exemplary embodiment, drive screw 104 is securely and rotateably held by housing 78 in a manner which places and holds drive screw 104 in a position wherein it is able to engage and drive beam 100 (as noted elsewhere herein, the second end 92 of flexible belt member 88 including drive beam 100 is also held within housing).

Thus, when patient interface device 70 is assembled as shown in FIGS. 12 and 14, the position of connecting member 22 of frame member 16 relative to forehead cushion support member 32 and forehead cushion 30 (which will be at a fixed position on the patient's head) can be adjusted by operation of the adjustment mechanism 76. In particular, rotation of knob member 104 will cause flexible belt member 88 to be moved within first support sleeve 80 (in the exemplary embodiment, the bottom portion of belt member will slide in a direction that is parallel to the longitudinal axis of connecting member 22). When this is done in a forward direction, it effectively lengthen the distance from the distal end of frame member 16 to forehead cushion support member 32. Since forehead cushion support member 32 and forehead cushion 30 are at a fixed position on the patient's head, such lengthening will cause the position of first support sleeve 80 relative to forehead cushion support member 32 and forehead cushion 30 to be changed, and as a result, previously bent portions of belt member 88 will be straightened (the associated notches 98 will close).

The reverse effect can be achieved by rotating knob member 108 in the other direction, effectively shortening the distance described above and causing previously straight portions of flexible belt member 88 to be bent (the associated notches 98 will open to allow for the bend). This selective adjustment thus allows for selective adjustment of the force that is applied to the bridge of the patient's nose by the apex portion of cushion 14 because varying the position of frame member 16 as just described will cause the apex portion of cushion 14 to rotate toward and away from the patient' nose.

Figure 15:
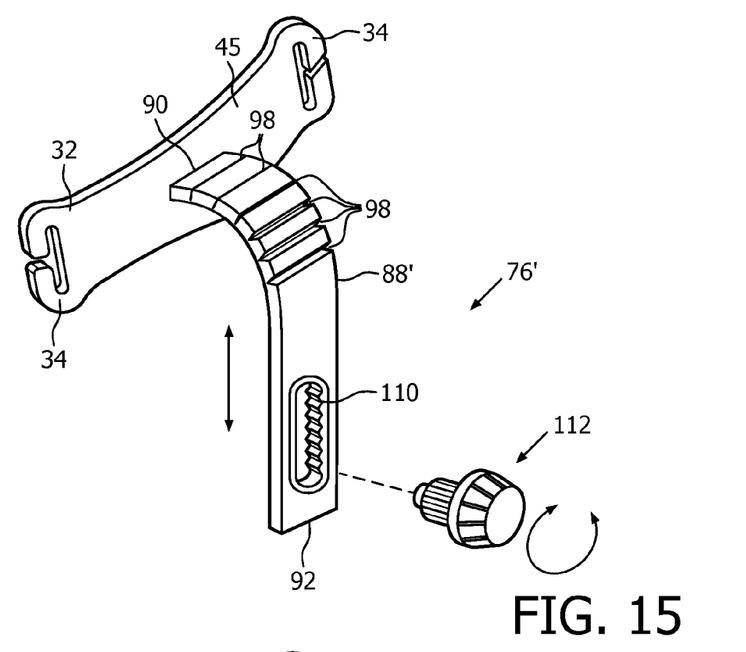
FIGS. 15-19 are schematic diagrams showing certain components of alternative adjustment mechanisms that may be used with the patient interface device of the system of FIG. 12.
Figure 16:
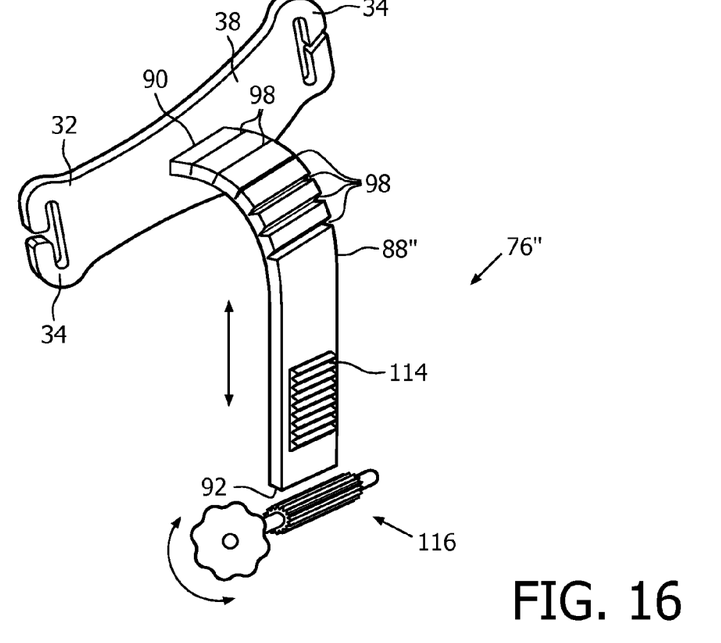
Figure 17:
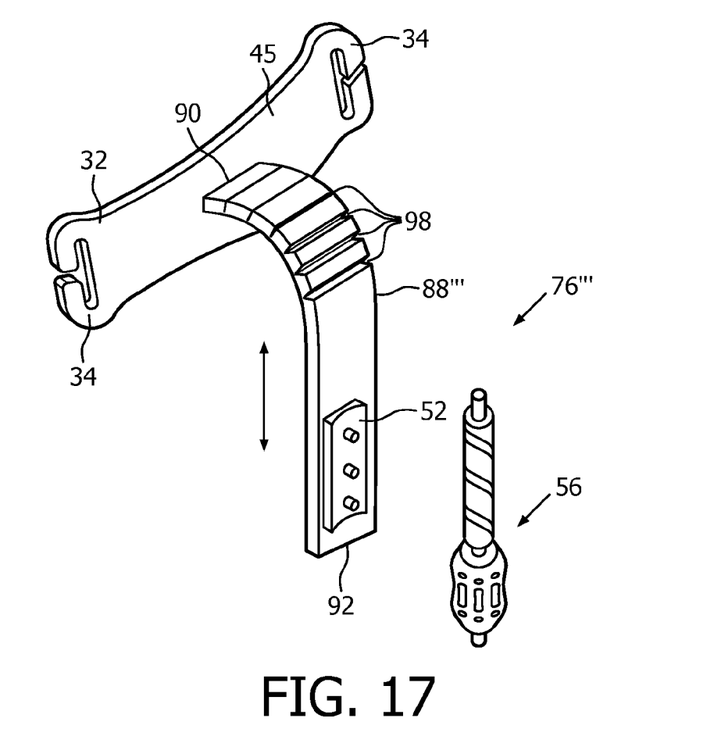

FIG. 15 is a schematic diagram showing certain components of an alternative adjustment mechanism 76' that may be substituted for adjustment mechanism 76. As seen in FIG. 15, adjustment mechanism 76' includes a belt member 88' having a one sided gear box 110 and a gear knob 112 in place of drive beam 100 and drive screw 104. FIG. 16 is a schematic diagram showing certain components of another alternative adjustment mechanism 76" that may be substituted for adjustment mechanism 76. As seen in FIG. 16, adjustment mechanism 76" includes a belt member 88" having a rack 114 and a pinion gear knob 116 in place of drive beam 100 and drive screw 104. FIG. 17 is a schematic diagram showing certain components of still another alternative adjustment mechanism 76''' that may be substituted for adjustment mechanism 76. As seen in FIG. 17, adjustment mechanism 76''' includes a flexible belt member 88''' having a drive beam 52 and a drive screw 56 as described elsewhere herein (FIG. 2) in place of drive beam 100 and drive screw 104.

Figure 18:
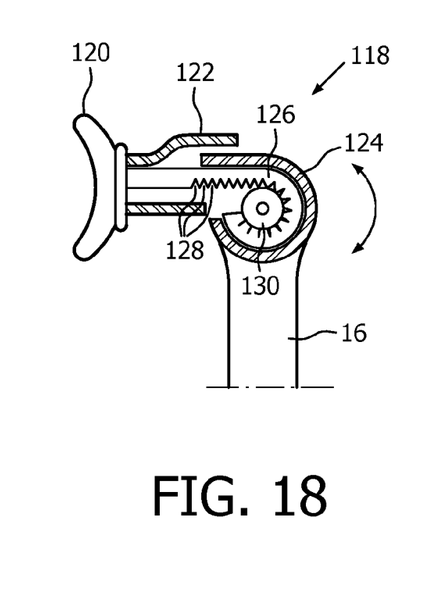

FIG. 18 is a side view of an adjustment mechanism 118 according to a further alternative embodiment that may be substituted for the other adjustment mechanisms described herein. Adjustment mechanism 118 includes a forehead cushion support member 120, a first sleeve 122 coupled to forehead cushion support member 120, and a second sleeve 124 coupled to a distal end of frame 16. Adjustment mechanism 118 also includes a flexible, serrated belt member 126 that is similar to flexible belt member 88. However, in belt member 126, notches 128 are normally spread open and are structured to close to enable it to be wound up as shown in FIG. 18. A rotatable drive screw 130 is coupled to second sleeve 124 and is structured to engage the notches 128 such that rotation of drive screw 130 will cause belt member 126 to be selectively wound and unwound, thereby changing the position of frame 16 relative to forehead cushion support member 120.

Figure 19:
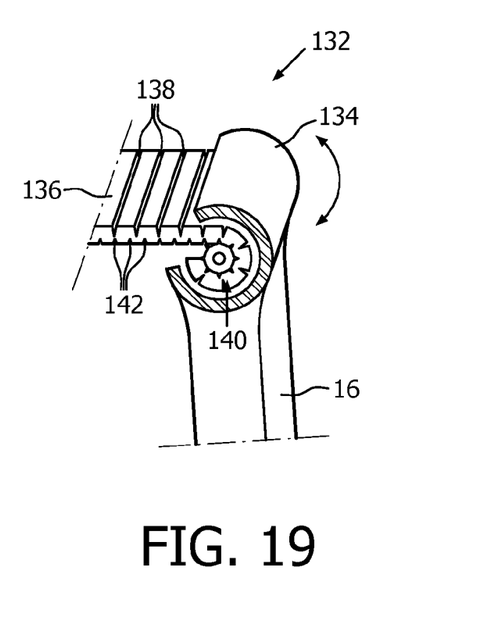

FIG. 19 is a partial side isometric view of an adjustment mechanism 132 according to still a further alternative embodiment that may be substituted for the other adjustment mechanisms described herein. Adjustment mechanism 132 includes a sleeve 134 coupled to a distal end of frame 16. Adjustment mechanism 132 also includes a flexible, serrated belt member 136 that is similar to flexible belt member 88. Belt member 136 includes notches 138 that are normally closed and are structured to be spread open to enable it to be wound up as shown in FIG. 19. A rotatable drive screw 140 is coupled to sleeve 128 and is structured to engage the notches 142 provided on a bottom surface of belt member 136 such that rotation of drive screw 140 will cause belt member 136 to be selectively wound and unwound, thereby changing the position of frame 16 relative to a forehead cushion support member to which the end of belt member 136 is attached.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
   a patient sealing assembly adapted to communicate a flow of breathing gas within an airway of a patient, the patient sealing assembly including a cushion and a frame member having a faceplate portion and an extension portion extending from the faceplate portion, the cushion being coupled to the faceplate portion;

a forehead member structured to engage a forehead of the patient;

a flexible elongated member having a first end portion and a second end portion, the first end portion being coupled to the forehead member and the second end portion being coupled to the extension portion of the frame member;

a drive assembly coupled to the second end portion of the flexible elongated member, the drive assembly being structured to selectively cause the second end portion of the flexible elongated member to move relative to the extension portion of the frame member in a first direction, wherein movement of the flexible elongated member relative to the extension portion in the first direction causes movement of the frame member relative to the forehead member in a second direction transverse to the first direction; and a shaping form, wherein the flexible elongated member is moveably received through the shaping form, wherein the shaping form is structured to change a shape of the flexible elongated member when the flexible elongated member is moved through the shaping form, and wherein movement of the flexible elongated member relative to the frame member in the first direction causes a selected portion of the flexible elongated member to move through the shaping form, wherein the shaping form includes a front surface and a rear surface, the rear surface being positioned closer to the forehead member than the front surface, wherein the flexible elongated member is a tubular member, wherein the shaping form is structured to change the shape of the selected portion from a generally flat shape to a generally rounded shape when the flexible elongated member is moved through the shaping form from the front surface to the rear surface.

2. The patient interface device according to claim 1, wherein when the patient interface device is donned by the patient, movement of the frame member relative to the forehead member will adjust a force applied to a bridge of a nose of the patient by an apex portion of the cushion by causing the cushion to pivot relative to the patient's nose.

3. The patient interface device according to claim 1, wherein the first direction is along a longitudinal axis of the extension portion of the frame member, the extension portion extending upwardly from the faceplate portion toward the patient's forehead when the patient interface device is donned by the patient.

4. The patient interface device according to claim 1, wherein the drive assembly comprises a first member provided on the second end portion of the flexible elongated member and a rotatable member operatively coupled to the first member, and wherein rotation of the rotatable member causes the flexible elongated member to move relative to the extension portion in the first direction.

5. The patient interface device according to claim 1, further comprising a first sleeve extending from the rear surface of the shaping form and a second sleeve extending from the forehead member, the flexible elongated member extending through the first sleeve and the second sleeve, wherein the first sleeve and the second sleeve are structured to move relative to each other and one within the other when the frame member moves relative to the forehead member in the second direction.

6. A patient interface device, comprising:

a patient sealing assembly adapted to communicate a flow of breathing gas within an airway of a patient, the patient sealing assembly including a cushion and a frame member having a faceplate portion and an extension portion extending from the faceplate portion, the cushion being coupled to the faceplate portion;

a forehead member structured to engage a forehead of the patient;

a flexible elongated member having a first end portion and a second end portion, the first end portion being coupled to the forehead member and the second end portion being coupled to the extension portion of the frame member;

a drive assembly coupled to the second end portion of the flexible elongated member, the drive assembly being structured to selectively cause the second end portion of the flexible elongated member to move relative to the extension portion of the frame member in a first direction, wherein movement of the flexible elongated member relative to the extension portion in the first direction causes movement of the frame member relative to the forehead member in a second direction transverse to the first direction; and a shaping form, wherein the flexible elongated member is moveably received through the shaping form, wherein the shaping form is structured to change a shape of the flexible elongated member when the flexible elongated member is moved through the shaping form, wherein the shaping form includes a front surface and a rear surface, the rear surface being positioned closer to the forehead member than the front surface wherein movement of the flexible elongated member relative to the frame member in the first direction causes a selected portion of the flexible elongated member to move through the shaping form, wherein the flexible elongated member is a tubular member, wherein the shaping form is structured to change the shape of the selected portion from a generally flat shape to a generally rounded shape when the flexible elongated member is moved through the shaping form from the front surface to the rear surface, wherein the generally flat shape is not self-supporting, and wherein the selected portion is self-supporting after moving through the shaping form.

7. A patient interface device, comprising:

a patient sealing assembly adapted to communicate a flow of breathing gas within an airway of a patient, the patient sealing assembly including a cushion and a frame member having a faceplate portion and an extension portion extending from the faceplate portion, the cushion being coupled to the faceplate portion;

a forehead member structured to engage a forehead of the patient;

a flexible elongated member having a first end portion and a second end portion, the first end portion being coupled to the forehead member and the second end portion being coupled to the extension portion of the frame member;

a drive assembly coupled to the second end portion of the flexible elongated member, the drive assembly being structured to selectively cause the second end portion of the flexible elongated member to move relative to the extension portion of the frame member in a first direction, wherein movement of the flexible elongated member relative to the extension portion in the first direction causes movement of the frame member relative to the forehead member in a second direction transverse to the first direction;

a shaping form, wherein the flexible elongated member is moveably received through the shaping form, wherein the shaping form is structured to change a shape of the flexible elongated member when the flexible elongated member is moved through the shaping form, wherein the shaping form includes a front surface and a rear surface, the rear surface being positioned closer to the forehear member than the front surface, wherein movement of the flexible elongated member relative to the frame member in the first direction causes a selected portion of the flexible elongated member to move through the shaping form, wherein the flexible elongated member is a tubular member, and wherein the shaping form is structured to change the shape of the selected portion from a generally flat shape to a generally rounded shape when the flexible elongated member is moved through the shaping form from the front surface to the rear surface, a support sleeve provided between the extension portion of the frame member and a front surface of the shaping form, wherein the second end portion of the flexible elongated member is slideably received within the support sleeve, and wherein movement of the flexible elongated member relative to the frame member causes the second end to slide within the support sleeve.

8. The patient interface device according to claim 7, further comprising a guide track housed within the support sleeve, wherein the second end portion of the flexible elongated member is slideably received within and supported by the guide track.

\* \* \* \* \*